United States Patent [19]

Rehmert, Jr.

[11] Patent Number: 5,075,320
[45] Date of Patent: * Dec. 24, 1991

[54] METHOD AND COMPOSITION FOR TREATING PARASITIC INFESTATION OF ANIMALS

[76] Inventor: Chalmer V. Rehmert, Jr., 10811 Edgefield Dr., San Antonio, Tex. 78233

[*] Notice: The portion of the term of this patent subsequent to Mar. 20, 2007 has been disclaimed.

[21] Appl. No.: 429,977

[22] Filed: Nov. 1, 1989

Related U.S. Application Data

[63] Continuation-in-part of Ser. No. 293,365, Jan. 4, 1989, Pat. No. 4,910,209.

[51] Int. Cl.$^5$ .......................................... A61K 31/445
[52] U.S. Cl. .................................................. 514/315
[58] Field of Search ........................................ 514/315

[56] References Cited

U.S. PATENT DOCUMENTS 4,822,608  4/1989  Benton et al. .................... 424/539

OTHER PUBLICATIONS

Chem. Abst. 98:54258g, 1983.
Chem. Abst. 93:168451s, 1980.
Chem. Abst. 105:227099z, 1986.
Chem. Abst. 106:33359j, 1987.

Primary Examiner—John W. Rollins
Attorney, Agent, or Firm—Gunn, Lee & Miller

[57] ABSTRACT

A method and composition for treating parasitic infestation of animals by the oral administration of a piperidine alkaloid composition over a period of days. Administration of Solenopsin A in an oral dosage form or whole body extract of the imported red fire ant, Solenopsis invicta, over a period of one to eleven days with regular booster dosages dissiminates the alkaloid composition through the blood and tissue fluids of the treated animals resulting in the elimination of blood and tissue-fluid feeding parasites.

2 Claims, No Drawings

METHOD AND COMPOSITION FOR TREATING PARASITIC INFESTATION OF ANIMALS

BACKGROUND OF THE INVENTION

This application is a continuation-in-part of copending U.S. Pat. application Ser. No. 293,365, filed Jan. 4, 1989, now U.S. Pat. No. 4,910,209.

This invention relates to a method and composition for treating animals with internal and external parasite infestation.

There are numerous flea, tick, and mite control products which involve external or topical treatment procedures including sprays, powders, dips and collars. Most of the existing products or procedures have proven largely ineffective with cats because of the cat's tendency to lick the product from its coat. Further, such topical products, which include pyrethrins and organophosphate insecticides under the brand names of Carbaryl, Malathion, Diazinon, and Dursban, have become increasingly less effective because the parasites have developed greater resistance to these products.

The applicant is aware of two products currently utilized for systemic treatment of ticks and fleas in dogs. These products are organophosphate insecticides under the brand names of Pro-Spot (13.8% fenthion), and Proban (cythioate) marketed by Haver, Mobay Corporation, Animal Health Division, Shawnee, Kansas 66201. Neither of these products are recommended for cats because of their toxicity. Organophosphate insecticides have been in use for some time for tick and flea control, but again, the parasites appear to be developing resistance to organophosphates and their efficacy has dropped off considerably.

The present invention offers an alternative to the known systemic parasite control products. Tests have shown the instant invention to be nearly 100% effective in eliminating flea and tick infestation. There have been no toxic effects on either dogs or cats tested. Hemograms and blood chemistries have remained normal in both dogs and cats.

SUMMARY OF THE INVENTION

The present invention is a method and composition for treating parasitic infestation in animals by the oral administration of a sufficient amount of a piperidine alkaloid composition to effectively control the parasitic infestation. Administration of Solenopsin A in oral dosage form or whole body extract of the imported red fire ant, Solenopsis invicta, over a period of days results in the elimination of ticks and fleas in both dogs and cats, without any toxic effects on the animals. This is particularly important in the systemic treatment of cats because of the toxicity of currently existing organophosphates to cats.

DETAILED DESCRIPTION OF THE PREFERRED EMBODIMENT

Considerable research has been done on the imported red fire ant, Solenopsis invicta. Chemical studies on the venom of this insect have shown that the veno is 95% alkaloids and the remaining 5% contains solubilized proteins and amino acids. The alkaloid fractions are characterized by the presence of various 2, 6 di-substituted piperidines. The venom also contains enzymes including hyaluronidase and phospholipase.

Of the piperidine alkaloids, Solenopsin A and Solenopsin B are the two major components with Solenopsin A being the primary component. Solenopsin A is a trans - 2 -methyl - 6 - n - undecylpiperidine. Solenopsin B is 2, 6 -trans - dialkyl - piperidine. Solenopsin A and Solenopsin B may be produced synthetically by any number of known techniques.

In one embodiment of the present invention, live fire ants are captured and quickly frozen to preserve their freshness. Each ant contains approximately 40 nanoliters of venom. For the further purposes of this disclosure, each ant is considered to comprise approximately one unit of venom or 40 nanoliters of venom containing the alkaloids Solenopsin A and Solenopsin B.

After freezing, the ants are ground to a fine texture, inserted into soluble capsules as whole body extract along with an edible carrier material, and kept frozen until administered to the animals, as will be discussed further.

While pure venom may be utilized in the treatment of parasite infestation it may be more practical from a commercial standpoint to use whole body extract. However, it is believed that the venom should be refrigerated in order to maintain the effectiveness of the product.

It is anticipated that the freshness of the alkaloid composition may be maintained through the use of appropriately coated capsules.

In treatment for parasitic infestation of dogs weighing 4 to 120 pounds, 100 to 400 units of whole body extract of Solenopsis invicta, containing the piperidine alkaloid composition including Solenopsin A and Solenopsin B, was orally administered over a period of 11 days. The first administration of 100 to 400 units occurred on day 1, day 2 was skipped to allow the animal to react to the dosage, and for nine consecutive days the animal was orally administered 100 to 400 units daily. Complete elimination of tick and flea infestation was achieved. No upper limit has been arrived at in terms of units that an animal may receive. A lower limit has not yet been determined, and may be more a function of the degree of severity of infestation.

Likewise, in the treatment for parasitic infestation of cats weighing 6 to 8 pounds, daily administration of 100-200 units of whole body extract of Solenopsis invicta over a period of 11 days resulted in complete elimination of flea infestation. The upper end limits of dosage for cats has not been reached, but in tests more than 400 units have not resulted in any ill effects. Again, no lower limit has been reached. To ensure that the treated animal is not reinfested, additional dosages in the range of 100-300 units are administered once monthly thereafter; i.e., a booster dose once monthly.

It is believed that when the piperidine alkaloid composition of the whole body extract of the imported red fire ant, Solenopsis invicta, containing Solenopsin A and Solenopsin B, is ingested by dogs and cats and other small animals, the piperidine alkaloid composition dissiminates through the blood and tissue fluids of the animal. When a flea, tick, mite, or other parasite obtains a blood or tissue fluid meal from the treated animal, the parasite's body structure and functions are destroyed within a few days by the Solenopsin A or Solenopsin B, resulting in death to the parasite. Since most parasites die before they have time to reproduce, infestation is rapidly eliminated.

Alternatively, recent studies have shown that synthetically produced Solenopsin is effective in the control of infestation of blood and tissue-fluid feeding parasites. Oral dosage capsule in the range of 1500 units are prepared by mixing 50-60 microliters of Solenopsin A with 0.1 ml of isopropylalcohol and 20 mg of fumed silica and 150 mg of microcrystalline cellulose as carrier materials. These are packaged in soluble capsules to form oral dosages for administration to the animals. (In these examples, again, one unit is approximately 40 nanoliters of Solenopsin A.) Any carrier which does not cause side-effects in the animal or which does not reduce the efficiency of the Solenopsin A is anticipated to be usable. With felines, it is anticipated that the Solenopsin A may be combined with fish oil as a carrier material since Solenopsin A is missible in such oils. Other edible oils may also be used.

Treatment of infested animals with Solenopsin A in an oral dosage form under a routine as described above for the whole body extract has resulted in nearly 100% elimination of blood and tissue-fluid feeding parasites. However, it appears that a higher number of units of Solenopsin A are required for effective treatment than when whole body extract of Solenopsis invicta is used. For example, current tests reveal that 1500 units of synthetic Solenopsin A gives the equivalent treatment of 250 units of whole body extract. In some tests in excess of 6000 units of synthetic Solenopsin A have been administered with no ill effects and the time frame for the treatment routine has been shortened.

One of the advantages of utilizing the Solenopsin A rather than whole body extract of Solenopsis invicta, is the synthetic Solenopsin A does not appear to need refrigeration to maintain its efficacy.

While the invention has been described in connection with a preferred embodiment, it is not intended to limit the invention to the particular form set forth, but, on the contrary, it is intended to cover alternatives, modifications, and equivalents, as may be included within the spirit and scope of the invention as defined by the appended claims.

What is claimed is:

1. A method for treating blood or tissue-fluid feeding parasite infestation of animals comprising the oral administration of a sufficient amount of Solenopsin A to effectively control said infestation.

2. A composition for treating blood or tissue-fluid feeding parasite infestation of animals comprising a sufficient amount of Solenopsin A and a carrier material of microcrystalline cellulose or edible oil in oral dosage form to effectively control said infestation when said composition is orally administered to said animal.

* * * * *